Figure 1:
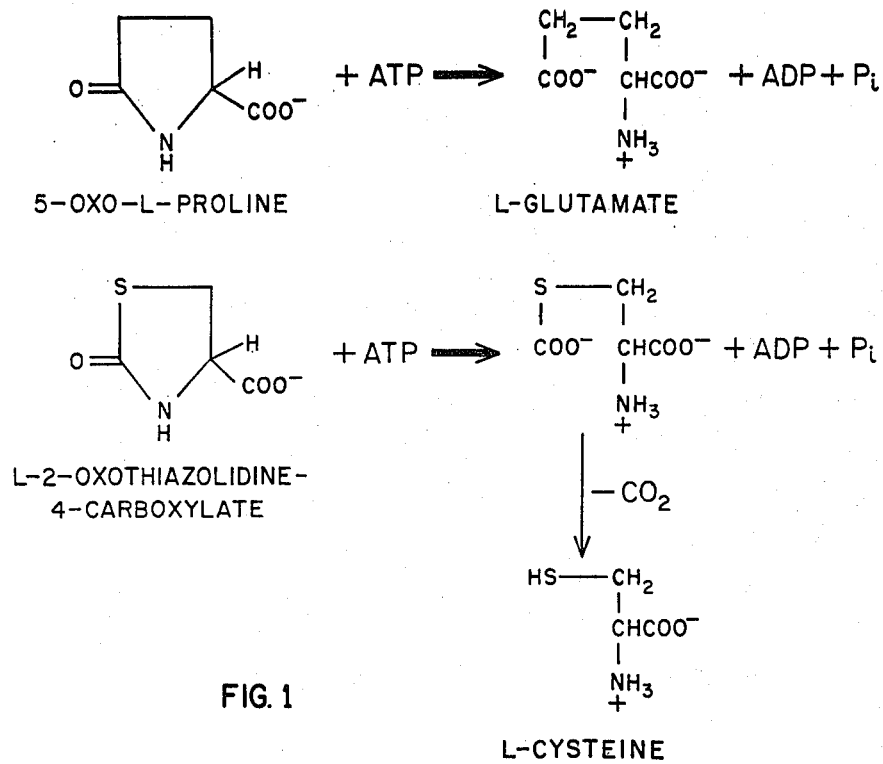

United States Patent [19]

Meister et al.

[11] 4,434,158

[45] Feb. 28, 1984

[54] CYSTEINE DELIVERY SYSTEM

[75] Inventors: Alton Meister, New York; Joanne M. Williamson, Roosevelt Island, both of N.Y.

[73] Assignee: Cornell Research Foundation, Ithaca, N.Y.

[21] Appl. No.: 368,903

[22] Filed: Apr. 15, 1982

Related U.S. Application Data

[62] Division of Ser. No. 233,564, Feb. 11, 1981, Pat. No. 4,335,210.

[51] Int. Cl.³ .................. A61K 37/54; A61K 31/195; A61K 31/425
[52] U.S. Cl. .................................... 424/94; 424/270; 424/319
[58] Field of Search ................ 435/113; 424/319, 424, 424/270

[56] References Cited

U.S. PATENT DOCUMENTS 4,255,446 3/1981 Iwao et al. .......................... 424/301
4,314,989 2/1982 Rosen .............................. 424/319 X Primary Examiner—Lionel M. Shapiro
Attorney, Agent, or Firm—Kenyon & Kenyon

[57] ABSTRACT

L-2-oxothiazolidine-4-carboxylate, a sulfur analog of 5-oxoproline, is cleaved by the enzyme 5-oxo-L-prolinase to form cysteine, thus providing the basis for a cysteine delivery system by the addition of L-2-oxothiazolidine-4-carboxylate to base amino acid solutions or by injecting it directly into in vivo cells.

1 Claim, 4 Drawing Figures

CYSTEINE DELIVERY SYSTEM

The United States of America has rights to this invention pursuant to Public Health Grant AM-12034.

This is a division of application Ser. No. 233,564, filed Feb. 11, 1981, now U.S. Pat. No. 4,335,210, issued June 15, 1982.

This invention relates to a novel cysteine delivery system.

Specifically, this invention relates to a novel base amino acid solution (given orally or parenterally) and to a novel procedure for the production of cysteine within living cells.

The invention provides a method of restoring the glutathione level of numerous tissues where 5-oxoprolinase is present, particularly the human liver. The invention also provides a method of combatting poisoning associated with the lessening or depletion of the glutathione content of cells. It is particularly applicable to the treatment of patients suffering from overdoses of acetoaminophenols.

The nature of the invention will be more readily understood from the description to follow.

THE CHEMISTRY INVOLVED

It is known that 5-oxo-L-prolinase (L-pyroglutamate hydrolase) catalyzes the adenosine triphosphate (ATP)-dependent cleavage of 5-oxo-L-proline to glutamate. The products of such cleavage viz., glutamate, ADP (adenosine diphosphate) and $P_i$ (inorganic ortho phosphate) are formed in a 1:1:1 ratio. It has now been found that a sulfur analog of 5-oxo-L-proline, viz, L-2-oxothiazolidine-4-carboxylate is also acted upon by this enzyme but the products include cysteine rather than glutamate. In the latter reaction the carboxylate is cleaved to yield an ADP/cysteine ratio of 1:1. The enzyme which exhibits an affinity for the analog similar to that for the natural substrate is inhibited by the anaalog, both in vitro and vivo. Thus, the carboxylate serves as a potent inhibitor of the gamma-glutamyl cycle at the step of 5-oxoprolinase. Administration of L-2-oxothiazolidine-4-carboxylate to mice that had been depleted of hepatic glutathione led to the restoration of normal hepatic glutathione levels. Since L-2-oxo-thiazolidine-4-carboxylate is an excellent substrate of the enzyme, it has been found to be useful as a component of base amino acid nutritional solutions and as an intracellular delivery system for cysteine. It is a good therapeutic agent for correcting conditions causing glutathione lessening or depletion, e.g., that resulting from poisoning induced by excessive amounts of acetaminophenol in the system.

The chemical reactions involved in the enzyme activity discussed above are shown in FIG. 1.

Figure 2:
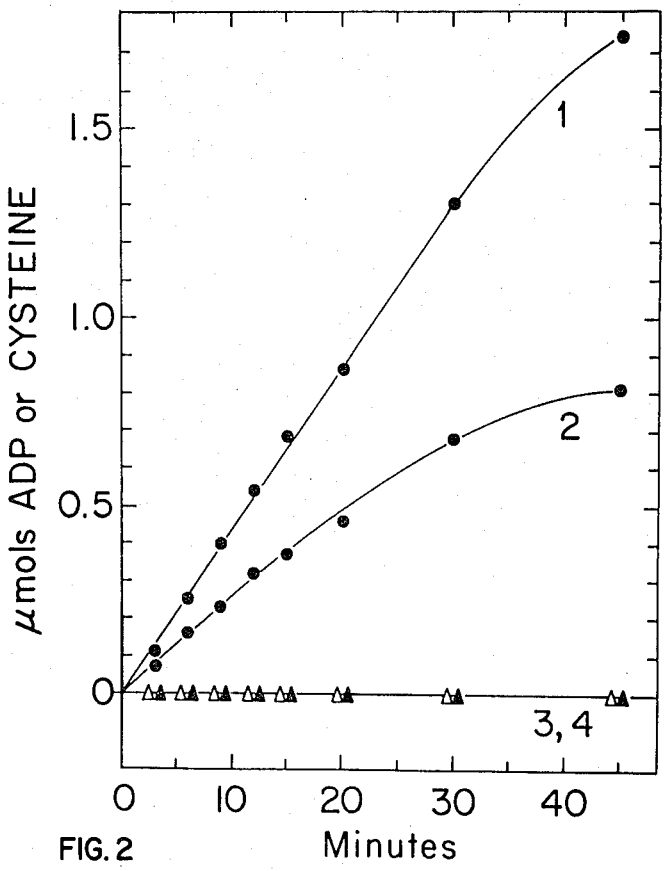

FIG. 2 is a chart showing the rate of formation of ADP and cysteine; and the absence of reaction when ATP was omitted or when the L-isomer was replaced with the D-isomer.

BASE AMINO ACID SOLUTIONS

Approximately 50% of hospitalized patients require some degree of nutritional support to counteract malnutrition and to assist in disease recovery. Many of such patients cannot take food directly because of G.I. tract dysfunction or poor oral intake. One of the primary means for establishing total parenteral nutrition is the infusion of basic amino acid solutions via central vein or peripheral vein administration. Typical base amino acid solutions contain eight essential amino acids and seven non-essential amino acids and are normally prepared and sold commercially in 10% aqueous solutions. Of the amino acids not contained in such solutions the most important is cysteine. As will be explained below, cysteine cannot be administered intravenously due to its toxic effects on the system. Cysteine is quite important to human metabolism since, of all the amino acids contained in the basic solutions, the only one containing sulphur is L-methionine. Methionine is metabolized only in the liver so that if a patient has a malfunctioning or partially functioning liver, his system becomes devoid of sulphur bearing protein. The present invention provides a method for introducing cysteine which can be metabolized as well in organs other than the liver.

In accordance with one aspect of this invention the basic amino acid solutions are modified by the incorporation therein of 0.25 to 2.5 g/dl (grams per deciliter)of L-2-oxothiazolidine-4-carboxylate. A typical standard crystalline amino acid injection(10 wt.% solution) for central vein administration contains the following ingredients:

| Essential Amino Acids | g/dl | Non-Essential Amino Acids | g/dl |
|---|---|---|---|
| L-Isoleucine | 0.720 | L-Alanine | 1.280 |
| L-Leucine | 0.940 | L-Arginine | 0.980 |
| L-Lysine (as (acetate salt) | 0.720 | L-Histidine | 0.300 |
|  |  | L-Proline | 0.860 |
| L-Methionine | 0.400 | L-Serine | 0.420 |
| L-Phenylalanine | 0.440 | L-Tyrosine | 0.044 |
| L-Threonine | 0.520 | Aminoacetic Acid (Glycine) | 1.280 |
| L-Tryptophan | 0.160 |  |  |
| L-Valine | 0.800 |  |  |

Another standard base amino acid solution for central vein administration contains only the essential amino acids in 5.3 wt. % concentration.

A standard base amino acid formulation for peripheral vein injection is a 3.5wt.% solution of the essential and non-essential amino acids and electrolytes, such as sodium, potassium, magnesium, chloride and acetate.

To the above nutrition support solutions there is added in accordance with this invention L-2-oxothiazolidine-4-carboxylate, preferably in the form of its neutral salt e.g., sodium, potassium, magnesium, etc., in the amount specified above.

EXPERIMENTS

In the experiments the reaction mixtures were made up to contain (final volume 0.5 ml) 100 mM Na Hepes (Na salt of N-2-hydroxyethylpiperizine-N'-2 ethanesulfonic acid) buffer (pH 8.0), 150 mM KCl, 8 mM $MgCl_2$, 2 mM phosphoenolpyruvate, 5 mM ATP (adenosine triphosphate), pyruvate kinase, in excess, 20 micrograms of 5-oxoprolinase, and the substrate as indicated.

The L- and D-isomers of 2-oxothiazolidine-4-carboxylate were synthesized by the method set out in Kaneko et al, Bull, Chem. Soc. (Japan) vol. 37, pp. 242-4 (1964) as modified by the method of Shah et al, Cancer Research vol. 39, pp. 3942-7 (1979). 5-Oxo-L-prolinase was isolated from rat kidney and freed of 5-oxoproline by gel filtration. Other chemicals and materials were obtained commercially.

After incubations for 30 min. at 37° C., the reaction mixtures were treated with 0.1 volume of 1 M HCl, and placed at 0° C. for 5 min.; and an equivalent volume of 1 M 2-amino-2-hydroxylmethyl-1,3,-propanediol was added. Portions were analyzed for amino acids by use of a Durrum Model 500 amino acid analyzer. Cysteine was also determined in some experiments by reaction with 5,5=-dithiobis (2-nitrobenzoate) (DTNB).

RESULTS

When the enzyme 5-oxo-L-prolinase was incubated with L-2-oxothiazolidine-4-carboxylate in the presence of ATP there was rapid formation of ADP and cysteine. Energy for the reaction is supplied by the cleavage of ATP. No reaction was observed when ATP was omitted or when the L-isomer was replaced by the corresponding D-isomer. The ratio of ADP to cysteine produced increased with time due undoubtedly to the loss of cysteine due to oxidation. A more quantitative characterization of the reaction was obtained in studies in which the formation of cysteine was estimated by determining derivatives of this amino acid product, wherein the formation of ADP and cysteine (determined, after oxidation, as cystine, or after reduction and derivatization as the corresponding S-acetamido compound) was found to be stoichiometric. It was noted that the apparent Km value for the L-isomer is somewhat lower than that found for the natural substrate, 5-oxo-L-proline; however, the calculated Vmax value for the natural substrate is higher than that found for the L-isomer. As expected, L-2-oxo-thiazolidine-4-carboxylate is an excellent inhibitor of the utilization of 5-oxo-L-proline by the purified enzyme; thus, in reaction mixtures containing 1 mM 5-oxo-L-proline, the addition of L-2-oxothiazolidine-4-carboxylate at concentration of 1, 5, and 10 mM produced 73, 92 and 97% inhibition of glutamate formation, respectively. Under these conditions D-2-oxothiazolidine-4-carboxylate did not inhibit glutamate formation. Utilizing reactions mixtures comparable to that described above tests were made on the natural substrate and on three substrate analogs. The results are summarized in the following table.

TABLE 1

Action of 5-Oxo-L-Prolinase on Substrates

| Substrate (conc., mM) | Products Formed ADP[a] | (nMoles) Amino Acid |
|---|---|---|
| 5-Oxo-L-proline (2) | 924 | 916[b] |
| L-2-oxothiazolidine-4-carboxylate (2) | 478<br>499 | 466[c]<br>463[d] |
| D-2-oxothiazolidine-4-carboxylate (5) | 96 | 0[c][e] |
| L-2-imidazolidone-4-carboxylate (2) | 930 | 0[f] |

[a]Determined by pyruvate kinase-lactate dehydrogenase coupled assay.
[b]as glutamate;
[c]determined after reduction with KBH4 and reaction with iodoacetamide;
[d]after conversion to cystine;
[e]less than 20 nmol;
[f]less than 5 nmol.

FIG. 2 shows graphically the results obtained with reaction mixtures similar to those of Table 1 except as follows: In Curves 1 and 2, 5 mM of the L-isomer and 5 mM ATP were contained; in Curve 3, 5 mM of the D-isomer and 5 mM ATP in Curve 4, 5 mM of the L-isomer but no ATP was added. At the indicated intervals portions were analyzed for ADP by the method indicated in the Table footnote, and for cysteine by reaction with DTNB.

The in vitro results showing that L-2-oxothiazolidine-4-carboxylate inhibits utilization of 5-oxoproline were confirmed by in vivo experiments. In the latter, animals were injected with 5-oxo-L-[$^{14}$C] proline and the respiratory [$^{14}CO_2$] produced was collected and measured for several hours. The results show that a marked decrease in the formation of [$^{14}CO_2$] occurred in the animals treated with L-isomer which excreted about 16% of the injected dose in their urine; no radioactivity was found in the urine of the controls. Upon injection of L-[$^{14}$C] glutamate to the animals the findings indicate that injection of L-2-oxothiazolidine-4-carboxylate does not have a significant effect on the metabolism of glutamate. Previous studies of the inventors showed that injection of another analog viz., L-2-imidazolidone-4-carboxylate also markedly inhibits the in vivo metabolism of 5-oxoproline, but not that of glutamate. However, L-2-oxothiazolidine-4-carboxylate is a much more efficient inhibitor. Comparison of the effects of the thiazolidine compound with those of L-2-imidazolidine-4-carboxylate indicate that the thiazolidine compound is at least four times more active on a molar basis.

ANIMAL STUDIES

The effect of injecting mice with L-2-oxothiazolidine-4-carboxylate on the level of hepatic glutathione was studied. The findings indicate that administration of the thiazolidine stimulated the formation of glutathione to levels that are about twice those of the controls. The maximal effect was observed about 4 hours after injection. No such stimulation was observed when the animals were injected with equivalent doses of D-2-oxothiazolidine-4-carboxylate. These findings are indicative of in vivo formation of cysteine after administration of L-2-oxothiazolidine-4-carboxylate. No free cysteine was detected in acid extracts of the livers of control or experimental animals by amino acid analyses carried out after reduction by dithiothreitol and derivatization with 2-vinylpyridine. This finding, not surprising in view of the very low levels of tissue cysteine, indicates that cysteine formed by cleavage of the thiazolidine is rapidly utilized for glutathione syntheses.

Figure 3:
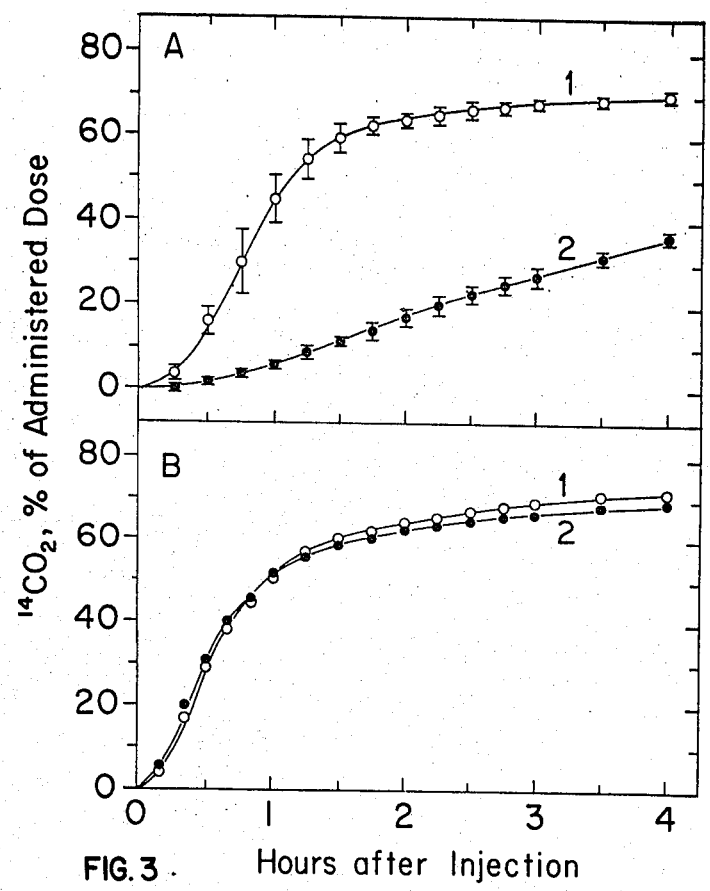

FIG. 3 depicts the inhibition of 5-oxoproline metabolsim by L-2-oxothiazolidine-4-carboxylate. Mice fasted overnight were injected intraperitoneally with NaCl (Curve 1; open symbols; controls) or with Na L-2-oxothiazolidine-4-carboxylate (2.5 mmol/kilo) (Curve 2; closed symbols). After 10 min., the mice were injected subcutaneously with 5-oxo-L-[$^{14}$C] proline (A) or with L-[$^{14}$C] glutamate (B) (0.02 mmol; $1.1 \times 10^6$ cpm). The mice were then placed in metabolic chambers and the respiratory $CO_2$ was collected in ethanolamine/methanol, 1:4 (vol/vol). In A, each curve represents the results on 3 animals; the points are mean values and the bars represent standard deviations from the mean. In B, each curve represents the average of closely-agreeing results obtained from 2 animals.

Figure 4:
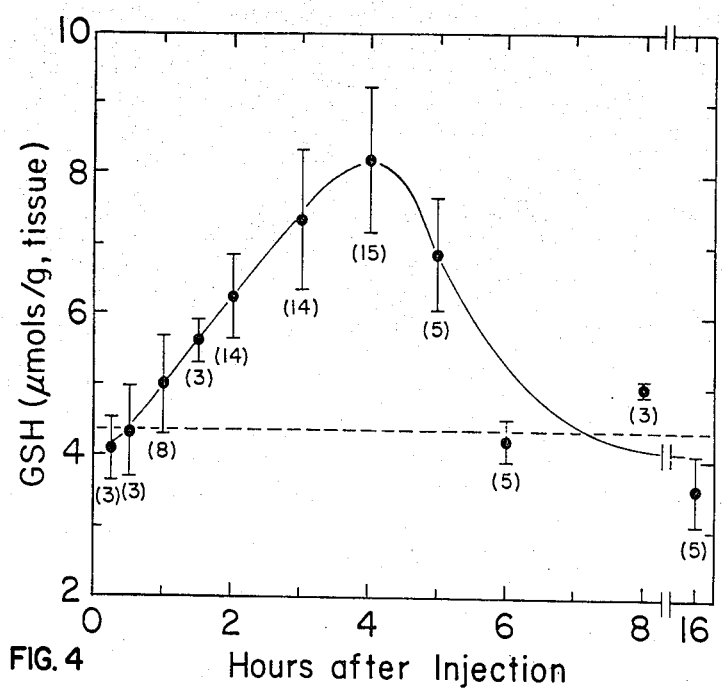

FIG. 4 shows the increase of hepatic levels of glutathione after injection of L-2-oxothiazolidine-4-carboxylate. Mice fasted overnight were injected intraperitoneally with NaCl (controls; dashed line) or with Na L-2-oxothiazolidine-4-carboxylate (6.5 mmol/kilo). At intervals, the mice were sacrificed and the excised liver was homogenized in 5 volumes of 1% picric acid. After centrifugation, the protein-free supernatant solutions were analyzed for glutathione by the method of Tietze, Anal. Biochem 27, 502–22(1969). Analyses were carried out in duplicate. In a number of instances, these values were checked by the 2-vinylpyridine procedure of Griffith, Anal. Biochem. 106; 207–12(1980); good agreement between the two methods was observed. In the figure, the points are mean values and the bars indicate the average deviation from the mean. The numbers in parentheses give the number of animals used. The value for the controls was 4.40±0.9 umol/g.

Administration of L-2-oxothiazolidine-4-carboxylate to animals leads to an increase in the cysteine content of tissues, especially the liver. Administration of this compound therefore provides a way of getting cysteine into cells. One cannot give cysteine itself without complications since this amino acid is toxic extracellularly. However, when the L-oxothiazolidine compound is injected it enters the cell where it is split giving rise to cysteine within the cell. In a number of clinical situations, for example, after poisoning with excessive pain-killing drugs, e.g., those containing active ingredients known as N-acetyl-para-aminophenol, paracetamol, and acetaminophen, the liver glutathione levels decrease markedly. When cysteine is supplied to liver cells, additional glutathione can be synthesized and thus serve usefully in detoxifying the offending drug. Therefore, L-2-oxothiazolidine-4-carboxylate serves as an intracellular delivery system for cysteine and has potential as a therapeutic agent in situations in which there is depletion of liver glutathione. After acetoaminophenol is given to experimental animals such as mice, the liver glutathione declines rapidly because it is extensively utilized by reaction with the drug. If one gives the L-isomer compound even two hours after the drug is given, an increase in liver glutathione occurs indicating the potential value of this compound in treatment. For human treatment the L-isomer, preferably in the form of its neutral salt is administered directly into the gastro-intestinal tract or introduced intravenously.

Having described the invention so that it may be practiced by those skilled in the art:

What is claimed is:

1. Method for increasing the glutathione level of an in vivo system which comprises administering to the system L-2-oxothiazolidine-4-carboxylate and subjecting it to the action of 5-oxo-L-prolinase in the presence of adenosine triphosphate to produce S-carboxy cysteine, decarboxylating S-carboxy cysteine to produce cysteine and metabolizing the latter to glutathione.

* * * * *